(12) United States Patent
Turner Kelly et al.

(10) Patent No.: US 11,690,992 B2
(45) Date of Patent: Jul. 4, 2023

(54) TACTILE FEATURES TO GUIDE USER INTERACTION WITH FLUID CONNECTOR

(71) Applicant: Becton, Dickinson and Company, Franklin Lakes, NJ (US)

(72) Inventors: Rachael Turner Kelly, Arlington, MA (US); Victor Isaac Politis, Natick, MA (US); Alex Chaves, Tyngsboro, MA (US); Gail Marie Siewiorek, Winchester, MA (US); Eric Bene, Middleton, MA (US); Attila Kiss, Tewksbury, MA (US); Megan Kohnen, University City, MO (US); Marc Hunter, Highland, IL (US); Laurie Bums, Town and Country, MO (US); Gail Hunter, Highland, IL (US); Max Ryan, St. Louis, MO (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 162 days.

(21) Appl. No.: 16/697,765

(22) Filed: Nov. 27, 2019

(65) Prior Publication Data

US 2020/0171294 A1      Jun. 4, 2020

Related U.S. Application Data

(60) Provisional application No. 62/773,662, filed on Nov. 30, 2018.

(51) Int. Cl.
*A61M 39/10*      (2006.01)
*A61M 39/28*      (2006.01)
*A61M 5/14*       (2006.01)

(52) U.S. Cl.
CPC .......... *A61M 39/10* (2013.01); *A61M 39/284* (2013.01); *A61M 5/14* (2013.01); *A61M 2205/582* (2013.01)

(58) Field of Classification Search
CPC ................ A61M 5/14; A61M 5/14244; A61M 5/14248; A61M 5/3137;
(Continued)

(56) References Cited

U.S. PATENT DOCUMENTS 4,072,311 A     2/1978  Bertucci
4,362,156 A  * 12/1982  Feller, Jr. .......... A61M 25/0637
                                                              604/165.03
(Continued)

FOREIGN PATENT DOCUMENTS

WO    WO-2009139857 A1    11/2009
WO    WO-2013086463 A4     6/2013

*Primary Examiner* — Kami A Bosworth
(74) *Attorney, Agent, or Firm* — Dickinson Wright PLLC

(57) ABSTRACT

A fluid connector, including a fluid path portion having an integral cannula extending in a first direction from a interior surface, and a latching portion secured to the fluid path portion and having a pair of displaceable arms. Each arm includes a connector latch disposed at a first cantilevered end of the arm, and an activation lever disposed at an opposite cantilevered end of the arm and extending in a second direction, not parallel to the first direction. A portion of the activation lever includes a first lateral tactile feature aligned substantially parallel to the first direction to prevent forward slippage of the fluid connector from a user's grasp in the second direction, and a portion of the activation lever includes a lateral tactile feature aligned substantially parallel to the second direction to prevent slippage of the fluid connector from a user's grasp in the first direction.

17 Claims, 11 Drawing Sheets

(58) Field of Classification Search
CPC ........... A61M 2005/14268; A61M 2005/1581;
A61M 2005/1587; A61M 2005/1586;
A61M 2005/3139; A61M 25/0637; A61M
2025/024; A61M 39/02; A61M 39/0202;
A61M 39/0205; A61M 39/0247; A61M
39/10; A61M 39/1055; A61M 39/284;
A61M 2039/027; A61M 2039/0276;
A61M 2039/0282; A61M 2039/1027;
A61M 2205/58; A61M 2205/582; A61M
2205/586
See application file for complete search history.

(56) References Cited

U.S. PATENT DOCUMENTS

| | | | | |
|---|---|---|---|---|
| 4,752,292 | A * | 6/1988 | Lopez | A61M 39/1011 604/244 |
| 5,968,011 | A * | 10/1999 | Larsen | A61M 5/158 604/164.01 |
| 6,302,866 | B1 * | 10/2001 | Marggi | A61M 25/0606 604/174 |
| 7,303,544 | B2 * | 12/2007 | Butikofer | A61M 25/02 604/93.01 |
| 10,531,834 | B1 * | 1/2020 | Smith | A61B 5/205 |
| 2002/0161332 | A1 * | 10/2002 | Ramey | A61M 5/158 604/180 |
| 2004/0158207 | A1 * | 8/2004 | Hunn | A61M 25/0612 604/164.01 |
| 2005/0101932 | A1 * | 5/2005 | Cote | A61M 5/158 604/506 |
| 2006/0030815 | A1 * | 2/2006 | Csincsura | A61M 5/158 604/93.01 |
| 2006/0224129 | A1 | 10/2006 | Beasley et al. | |
| 2007/0073270 | A1 * | 3/2007 | Christensen | A61M 25/0075 604/533 |
| 2007/0185441 | A1 * | 8/2007 | Fangrow, Jr. | A61M 25/0612 604/93.01 |
| 2007/0276344 | A1 | 11/2007 | Bizup et al. | |
| 2008/0249471 | A1 * | 10/2008 | DeStefano | A61M 25/02 604/164.01 |
| 2009/0143763 | A1 * | 6/2009 | Wyss | A61M 5/158 604/164.11 |
| 2009/0287140 | A1 * | 11/2009 | Rittman, III | A61B 90/11 604/21 |
| 2010/0317999 | A1 * | 12/2010 | Shaw | A61B 5/15003 600/576 |
| 2012/0029483 | A1 * | 2/2012 | Griffith | A61J 15/0092 604/535 |
| 2012/0157924 | A1 * | 6/2012 | Schutz | A61M 5/158 604/175 |
| 2014/0316379 | A1 * | 10/2014 | Sonderegger | A61M 5/142 604/506 |
| 2015/0105753 | A1 * | 4/2015 | Okiyama | A61M 39/045 604/535 |
| 2017/0209682 | A1 * | 7/2017 | Shemesh | A61M 39/10 |
| 2018/0133451 | A1 * | 5/2018 | Takeuchi | F16L 37/133 |
| 2021/0236724 | A1 * | 8/2021 | Marggi | A61M 5/158 |

* cited by examiner

TACTILE FEATURES TO GUIDE USER INTERACTION WITH FLUID CONNECTOR

CROSS-REFERENCE TO RELATED APPLICATION

This application claims priority under 35 USC § 119(e) from U.S. Provisional Application No. 62/773,662, filed on Nov. 30, 2018, the disclosure of which is incorporated herein by reference in its entirety.

FIELD OF THE INVENTION

The present invention relates generally to infusion devices, and more particularly, to infusion devices to be used in conjunction with an infusion pump in the subcutaneous infusion of insulin and other medicaments.

BACKGROUND OF THE INVENTION

One mode of insulin infusion treatment includes infusion pump therapy via a catheter, needle, or other type of cannula. Infusion pumps offer the advantages of continuous infusion of insulin, precision dosing, and programmable delivery schedules. Together, these advantages result in more accurate blood glucose control. In this mode of insulin infusion treatment, the infusion pump remains attached to the user and required doses of insulin are delivered to the user via the pump.

One type of cannula is a catheter, which generally is a tube that can be inserted into the body to permit the administration of fluids. In infusion pump therapy, the types and sizes of the catheter may vary, but generally, the catheter is a thin, flexible tube. In some uses, however, it may be larger and/or rigid. A rigid, hollow, metal needle may also be used in place of a soft plastic catheter.

One type of conventional infusion set is sold as the Quick-Set® infusion set by Medtronic. In such devices, the infusion pump includes a catheter assembly connected to a pump via a tubing set, and a separate insertion device inserts and/or attaches the catheter assembly into/to a user via an introducer needle provided as part of the infusion set. The infusion set and insertion device can also be combined, as in the Mio® infusion set sold by Medtronic, which is an "all-in-one" design that combines the infusion set and insertion device into one unit.

Another type of insulin infusion device, known as a "patch pump," has recently become available. Unlike a conventional infusion pump, a patch pump is an integrated device that combines most or all of the fluid components in a single housing that is adhesively attached to an infusion site, and does not require the use of a separate infusion (tubing) set. A patch pump adheres to the skin, contains insulin (or other medication), and delivers the drug over a period of time, either transdermally, or via an integrated subcutaneous mini-catheter. Some patch pumps communicate with a separate controller device wirelessly (such as one sold under the brand name OmniPod®), while others are completely self-contained.

A conventional infusion device can include a fluid connector, which may be releasably attached to a base that can be secured to a user's skin. An infusion pump supplies fluid to a catheter via the fluid connector/base engagement.

With such devices, however, there are concerns over the difficulty of balancing the force required to disconnect the tubing without pulling the catheter from the user's skin versus having enough retention force to secure the infusion components for everyday infusion. Another concern is that the separation force needs to be designed such that if a user accidentally snags the extension tubing on an external structure (e.g., a doorknob), the extension tubing will disconnect from the fluid connector without removing the catheter from the user's skin, thus saving the patient from the need to obtain, connect and re-insert a new infusion set. Yet another concern is the ability of patients, many with reduced tactile sensation, to properly and reliably connect and disconnect fluid connectors from bases.

SUMMARY OF EMBODIMENTS OF THE INVENTION

Accordingly, it is an aspect of the present invention to provide a fluid connector that is easy to connect and disconnect from a base.

The foregoing and/or other aspects of the present invention are achieved by providing a fluid connector for use with an infusion set. The fluid connector includes a housing having a cannula integral with and extending distally from a proximal interior surface of the housing. A proximal exterior surface of the housing has a flattened portion with a raised tactile feature centered about a longitudinal axis of the cannula to aid a user in connecting the fluid connector with an infusion set base.

The foregoing and/or other aspects of the present invention are also achieved by providing a two-piece fluid connector for use with an infusion set. The fluid connector includes a fluid path portion, including a cannula integral with and extending from a proximal interior surface of the fluid path portion. The fluid connector also includes a latching portion secured to the fluid path portion and having a pair of displaceable arms. Each displaceable arm includes a connector latch disposed at a first, cantilevered end of the arm, and an activation lever disposed at an opposite cantilevered end of the arm. A proximal portion of the activation lever includes a raised lateral tactile feature to prevent distal slippage of the fluid connector from a user's grasp.

The foregoing and/or other aspects of the present invention are also achieved by providing a two-piece fluid connector for use with an infusion set. The fluid connector includes a fluid path portion, including a cannula integral with and extending from a proximal interior surface of the fluid path portion. The fluid connector also includes a latching portion secured to the fluid path portion and having a pair of displaceable arms. Each displaceable arm includes a connector latch disposed at a first, cantilevered end of the arm, and an activation lever disposed at an opposite cantilevered end of the arm. A rearmost portion of the activation lever includes a raised lateral tactile feature to prevent forward slippage of the fluid connector from a user's grasp.

Additional and/or other aspects and advantages of the present invention will be set forth in the description that follows, or will be apparent from the description, or may be learned by practice of the invention.

BRIEF DESCRIPTION OF THE DRAWINGS

The above and/or other aspects and advantages of embodiments of the invention will be more readily appreciated from the following detailed description, taken in conjunction with the accompanying drawings, in which.

DETAILED DESCRIPTION OF EMBODIMENTS OF THE PRESENT INVENTION

Figure 1:
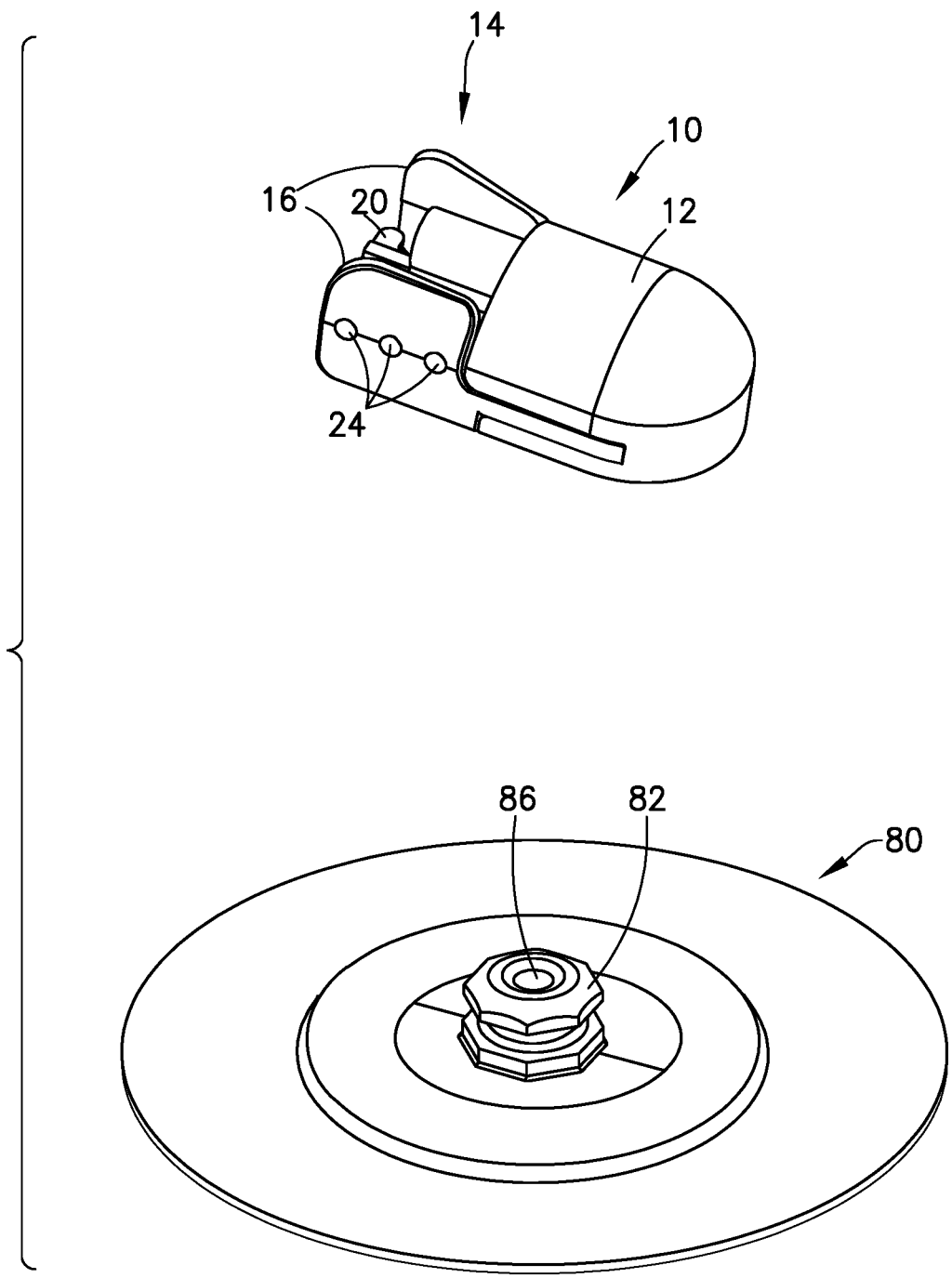
FIGS. 1-4 are various views of a related art fluid connector and an associated base.

Reference will now be made in detail to embodiments of the present invention, which are illustrated in the accompanying drawings, wherein like reference numerals refer to like elements throughout. The embodiments described herein exemplify, but do not limit, the present invention by referring to the drawings.

The embodiments are not intended to be mutually exclusive; features of one embodiment can be combined with other embodiments as long as they do not contradict each other.

It will be understood by one skilled in the art that this disclosure is not limited in its application to the details of construction and the arrangement of components set forth in the following description or illustrated in the drawings. The embodiments herein are capable of other embodiments, and capable of being practiced or carried out in various ways. Phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled"" and variations thereof are not restricted to physical or mechanical connections or couplings. Further, terms such as "up," "down," "bottom," "top," "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those skilled in the art to refer to reasonable ranges around and including the given value and ranges outside the given value, for example, general tolerances associated with manufacturing, assembly, and use of the embodiments. The term "substantially" when referring to a structure or characteristic includes the characteristic that is mostly or entirely.

Figure 2:
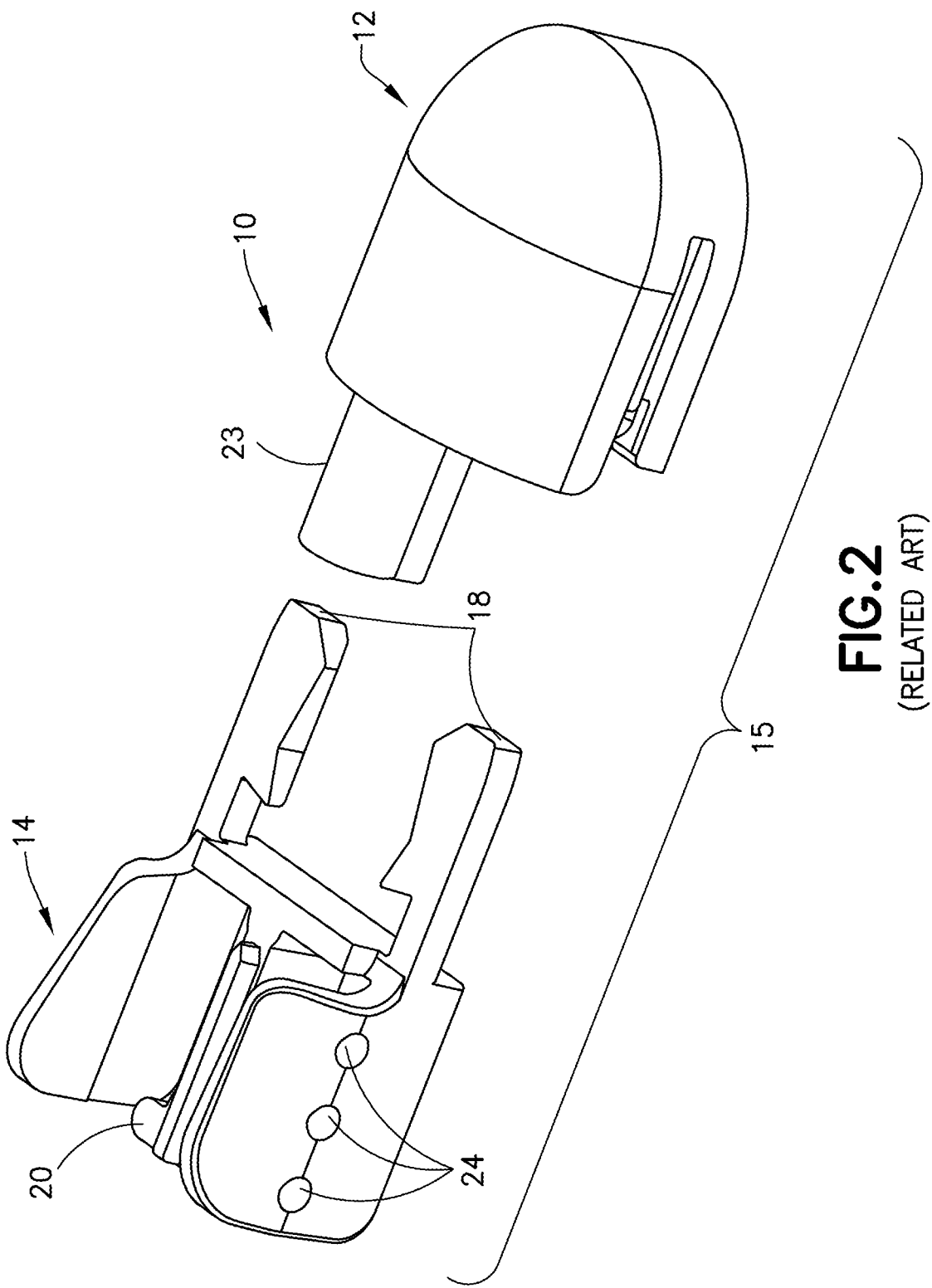
Figure 3:
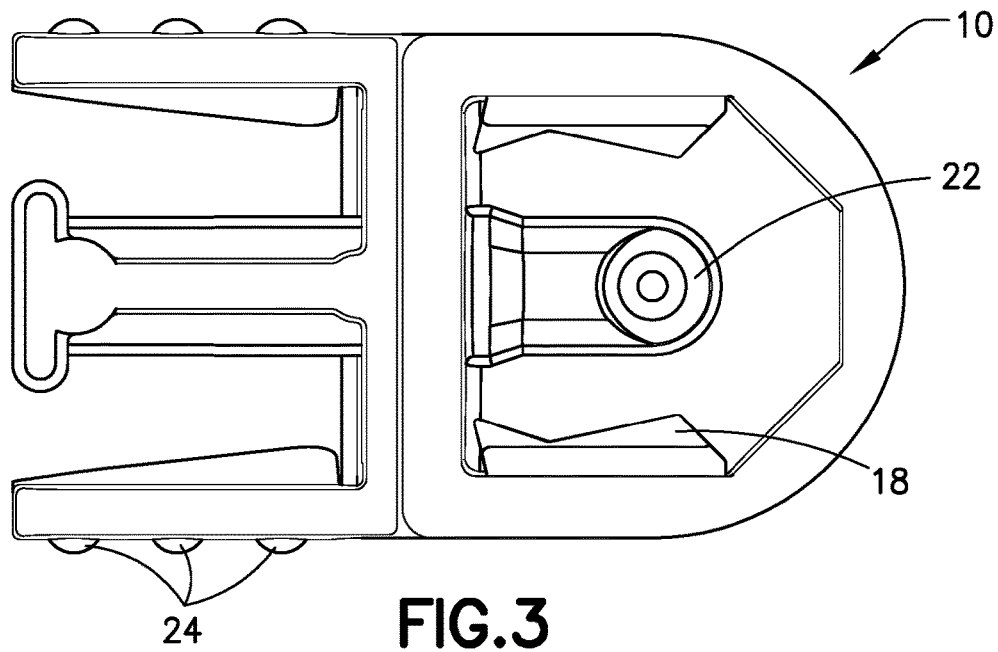
Figure 4:
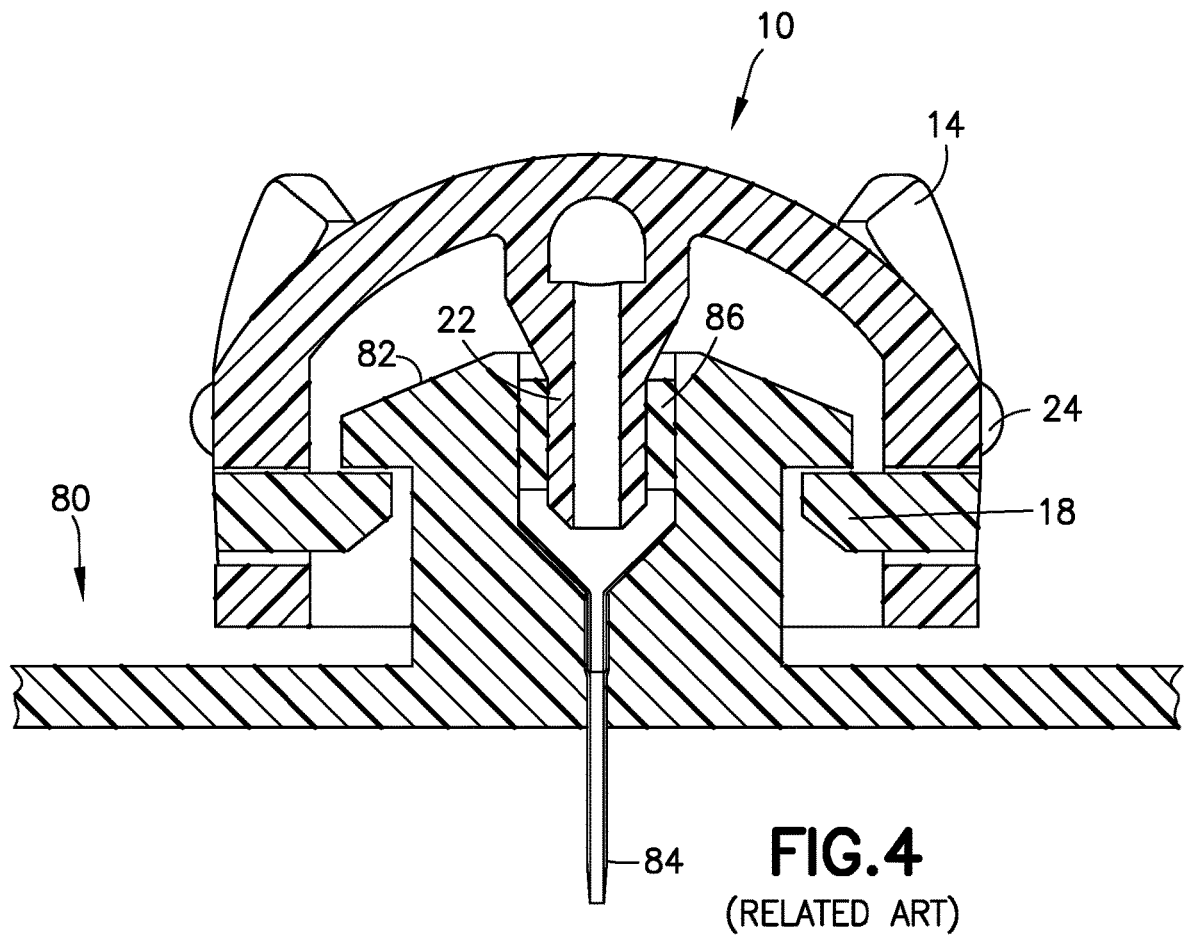

FIG. 1 is a perspective view of a related art two-piece fluid connector 10 and associated base 80, such as those found in WO 2013/086463, the disclosure of which is incorporated herein by reference in its entirety. FIG. 2 is an exploded perspective view of the fluid connector 10, FIG. 3 is a bottom view of the fluid connector 10, and FIG. 4 is a cross-sectional view of the fluid connector 10 connected with the base 80. The fluid connector 10 includes two components: a fluid path portion 12, and a latching portion 14. Together, the fluid path portion 12 and the latching portion 14 form a housing 15. The latching portion 14 includes activation levers 16, fluid connector latches 18, and a rigid stop 20.

The activation levers 16, fluid connector latches 18, and the rigid stop 20 are integrally formed as a unitary structure. Additionally, the activation levers 16 form arms with their respective fluid connector latches 18. These arms are displaceable relative to the fluid path portion 12. The fluid connector latches 18 are displaceable to a latching position in which at least a portion of the fluid connector latch 18 is disposed within the fluid path portion 12. Further, the arms are resiliently biased toward the latching position.

As best shown in FIGS. 1 and 4, a top surface of the fluid connector 10 is rounded to reduce the profile and minimize potential snagging when worn by a user.

The fluid path portion 12 includes a tubing connector portion 23 for connecting the fluid connector 10 with tubing. The fluid path portion 12 can be secured to the latching portion 14 via snap-fit engagement.

As shown in FIGS. 1, 3 and 4, the fluid path portion 12 has a blunt cannula 22 extending distally from a proximal interior surface of the housing 15. When connected to a corresponding base 80 with a patient cannula 84 that has been inserted into the user's skin, the blunt cannula 22 pierces a septum 86 in a mushroom-shaped head 82 of the base 80 to fluidly connect a pump with the patient cannula 86 on the distal side of the base 80.

Preferably, the user attaches the fluid connector 10 to the corresponding base 80 by pressing distally (i.e., straight down), forcing the fluid connector latches 18 outward due to contact with the mushroom-shaped head 82 of the base 80, and snapping the fluid connector 10 in place once the fluid connector latches distally bypass the mushroom-shaped head 82 due to the inward resilient bias of the fluid connector latches 18.

To release the fluid connector 10 from the base 80, the user squeezes the activation levers 16, for example, until they contact the rigid stop 20. This action disengages the fluid connector latches 18 from the mushroom-shaped head 82 of the base 80 by pivoting and displacing the fluid connector latches 18 radially outward sufficiently to clear the mushroom-shaped head 82. Then, the user lifts the fluid connector 10 proximally off the base 80.

The activation levers 16 can have finger bumps 24 centrally located thereon to aid the user in locating and using the activation levers 16.

But many users may have reduced tactile function in their fingers, and a small size of the fluid connector 10 can make connection with the base 80 difficult. Additionally, with the rounded surface of the fluid connector 10, a user's fingers can potentially slip when gripping the fluid connector. Further, many fluid connectors on the market connect to a base by sliding horizontally (i.e., substantially parallel to the skin surface) or at a non-vertical angle. Thus, the vertical connection of the fluid connector 10 with the base 80 may be unfamiliar to users. The fluid connector 10 itself does not indicate how to connect the fluid connector 10 to the base 80.

Further, the central location of the finger bumps 24 on the rounded activation levers 16 can potentially result in slippage of a user's fingers.

Figure 5:
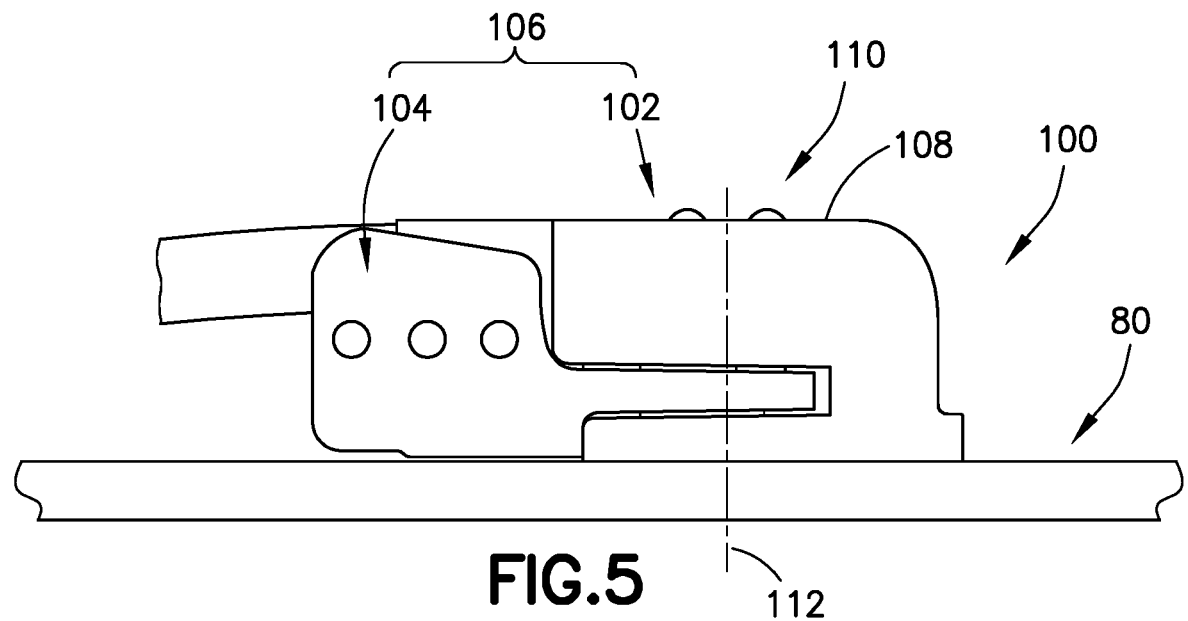
FIG. 5 is a side elevation view of a fluid connector in accordance with an embodiment of the present invention connected with a base.
Figure 6:
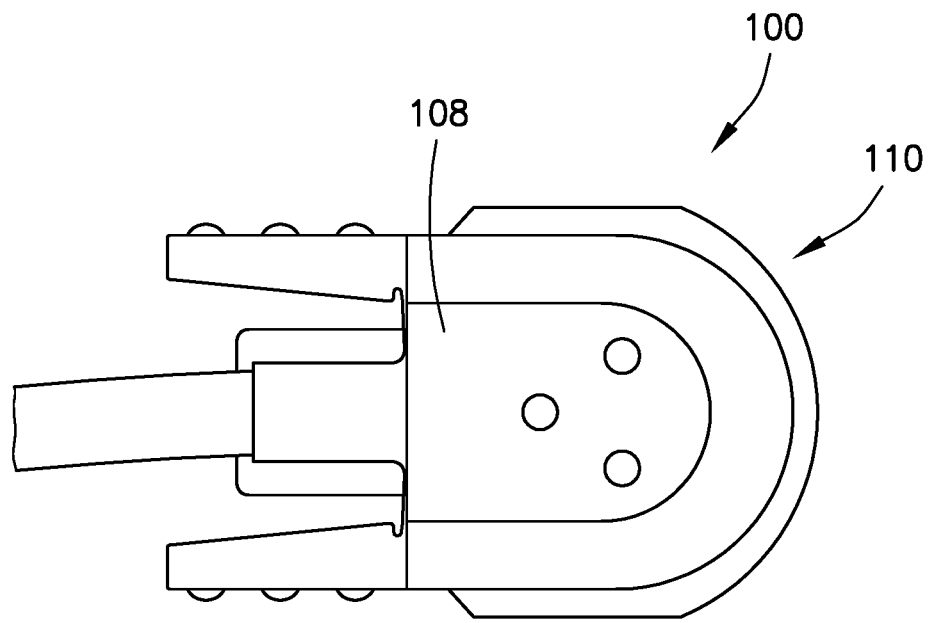
FIG. 6 is a top view of the fluid connector of FIG. 5.

FIG. 5 is a side elevation view of a fluid connector 100 in accordance with an embodiment of the present invention connected with a base, such as the base 80. FIG. 6 is a top view of the fluid connector 100. Together, a fluid path portion 102 and a latching portion 104 form a housing 106. The latching portion 104 is omitted from FIG. 7, which is a perspective view of the fluid path portion 102. Although not explicitly depicted, like the previously described housing 15, the housing 106 has a blunt cannula (substantially the same as blunt cannula 22 shown in FIGS. 3 and 4, and omitted for brevity) extending distally from a proximal interior surface of the housing 106. The blunt cannula has a longitudinal axis 112 shown in FIG. 5.

Figure 7:
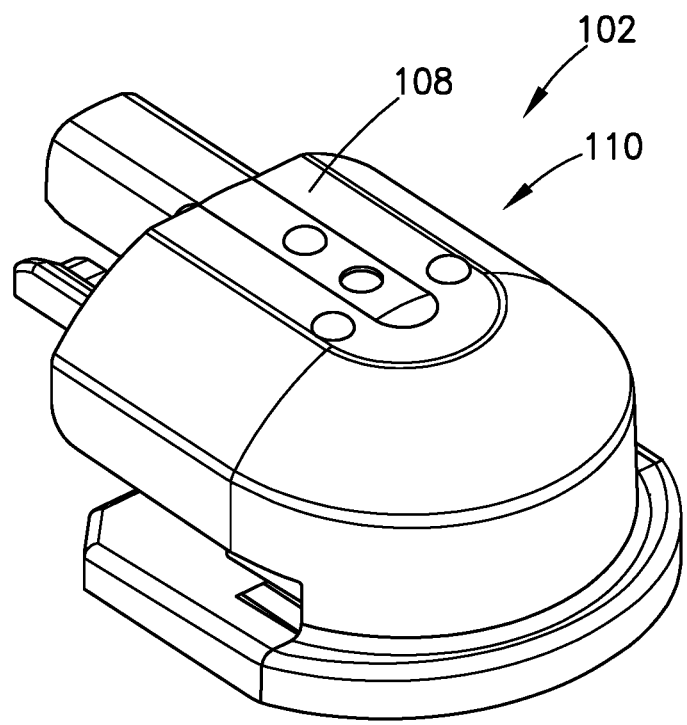
FIG. 7 is a perspective view of a fluid path portion of the fluid connector of FIG. 5.

As shown in FIGS. 5-7, rather than a rounded top surface like that of fluid connector 10, a proximal exterior surface of the fluid path portion 102 has a flattened portion 108 that has a raised tactile feature 110. According to one embodiment, the raised tactile feature 110 is centered about the longitudinal axis 112 of the blunt cannula. The raised tactile feature 110 provides an aid to the user in connecting the fluid connector 100 to the base 80 because it tactilely informs the user of the position of the longitudinal axis of the cannula and therefore, informs the user of the location to center the fluid connector 10 over the base 80 and to press down on the fluid connector 10 for making the connection with the base 80.

Figure 8:
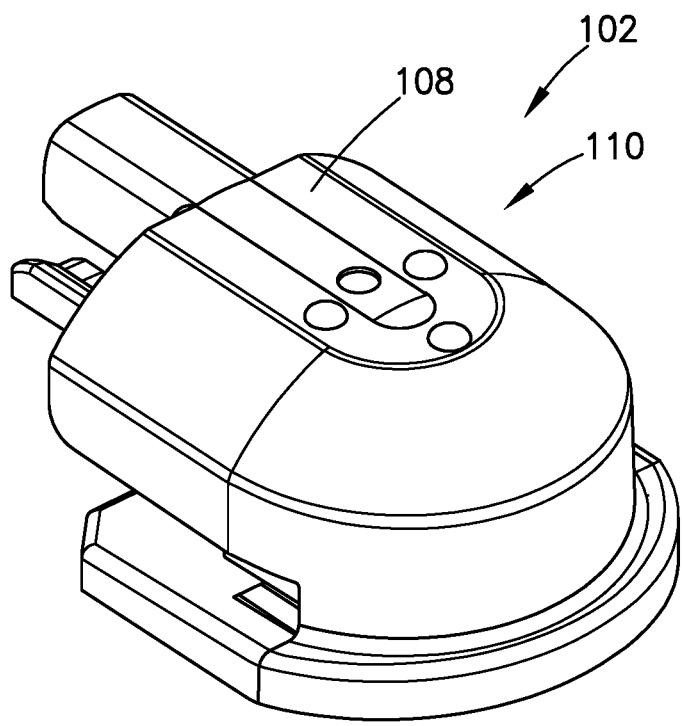
FIG. 8 is a perspective view of a fluid connector in accordance with another embodiment of the present invention.

According to one embodiment, as shown in FIGS. 5-7, the raised tactile feature 110 is three bumps arranged in a triangle centered about the longitudinal axis 112 of the cannula. In FIG. 8, the raised tactile feature 110 is also three bumps arranged in a triangle centered about the longitudinal axis 112 of the cannula, but the orientation of the triangle is inverted with respect to the orientation of the triangle in FIG. 7.

Figure 9:
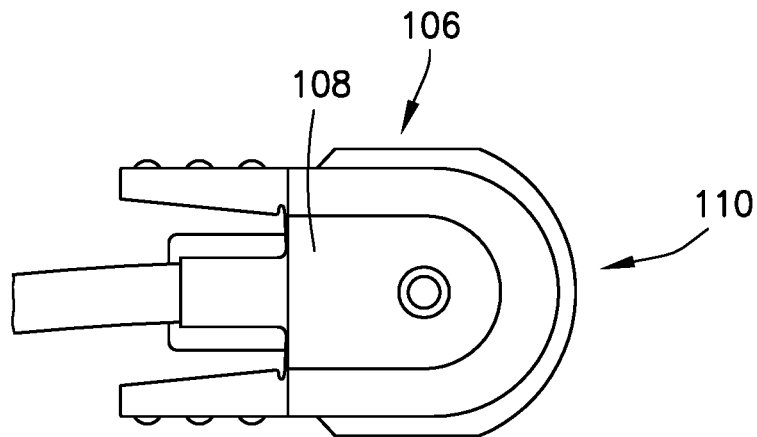
FIGS. 9-17 are respective top views of fluid connectors in accordance with other embodiments of the present invention.
Figure 10:
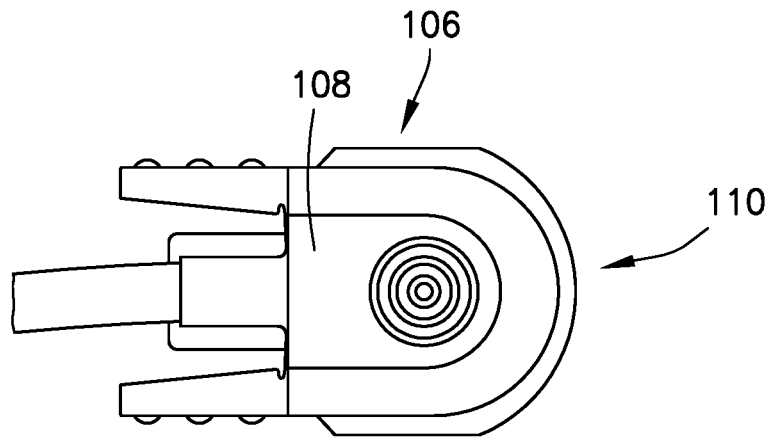
Figure 11:
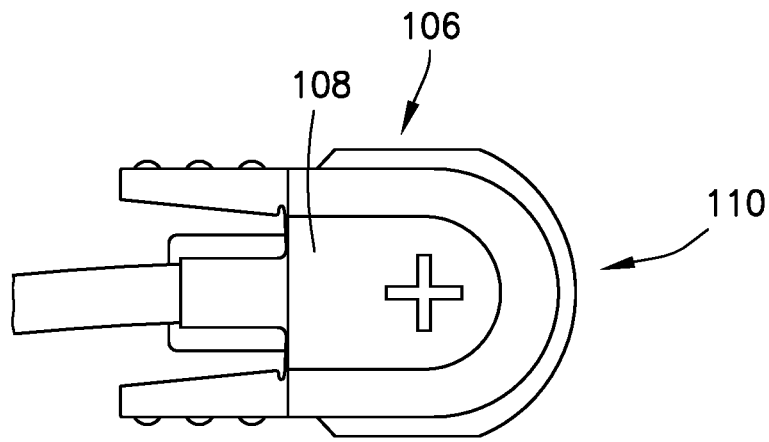
Figure 12:
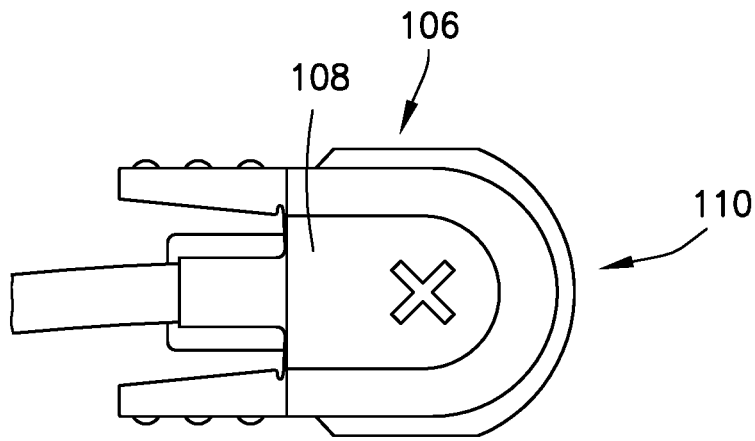
Figure 13:
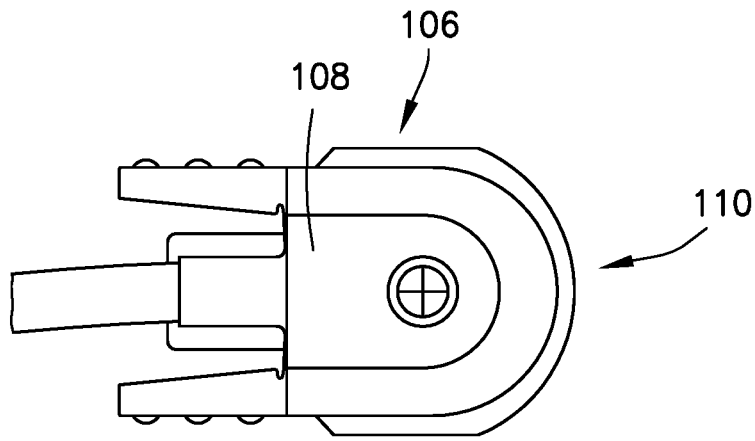

FIGS. 9-17 are respective top views of fluid connectors in accordance with other embodiments of the present invention. In each of these embodiments, the raised tactile feature is centered about the longitudinal axis 112 of the cannula. In FIG. 9, the raised tactile feature 110 is a ring, and in FIG. 10, the raised tactile feature is a plurality of concentric rings. In FIG. 11, the raised tactile feature 110 is a cruciform or cross-shape or cross, and in FIG. 12, the raised tactile feature 110 is an "X." The raised tactile feature 110 in FIG. 13 is crosshairs.

Figure 14:
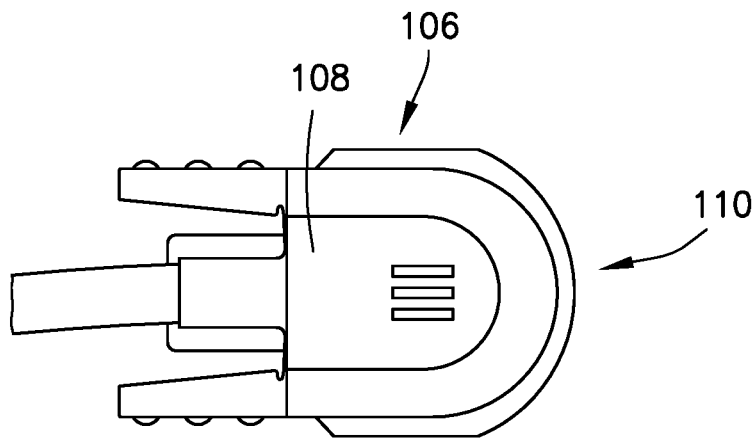
Figure 15:
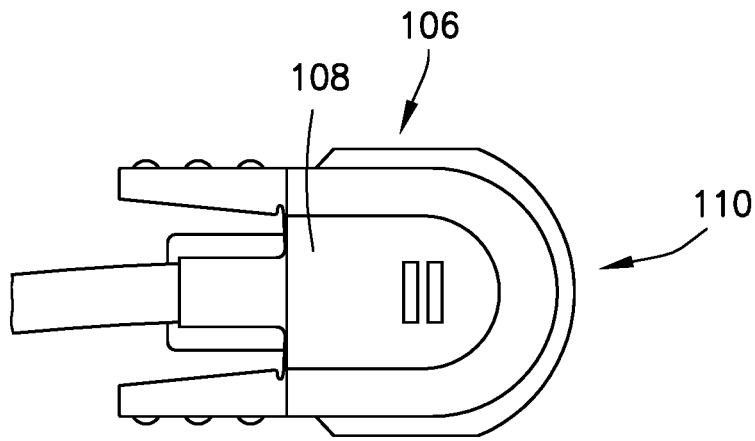

In FIGS. 14 and 15, the raised tactile feature 110 is a plurality of linear ribs. In FIG. 14, the linear ribs are oriented to run front to back of the housing 106, and in FIG. 15, the linear ribs are oriented to run laterally. One skilled in the art will appreciate that other orientations of the linear ribs are possible without departing from the present invention's scope.

Figure 16:
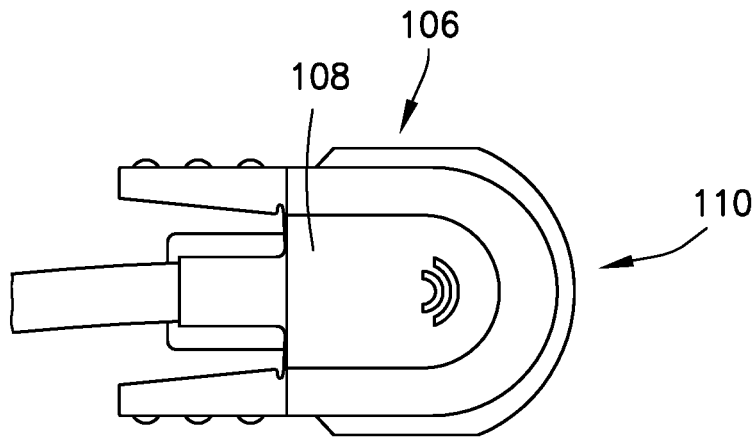
Figure 17:
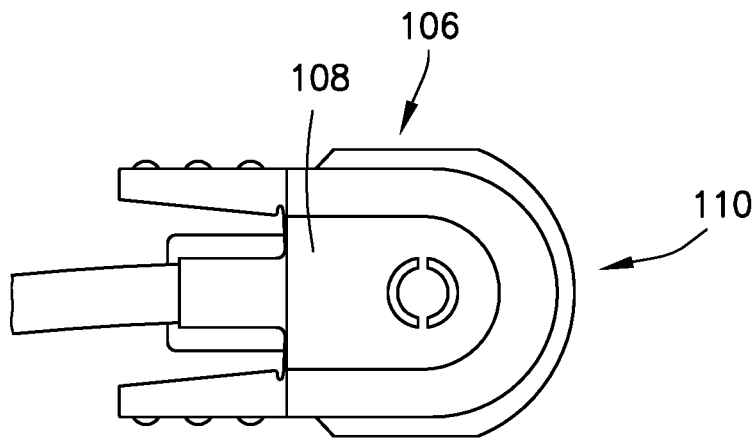

In FIGS. 16 and 17, the raised tactile feature 110 is a plurality of arcuate ribs. In FIG. 16, the arcuate ribs are oriented in the same direction, and in FIG. 17, the arcuate ribs are oriented in different directions.

Figure 18:
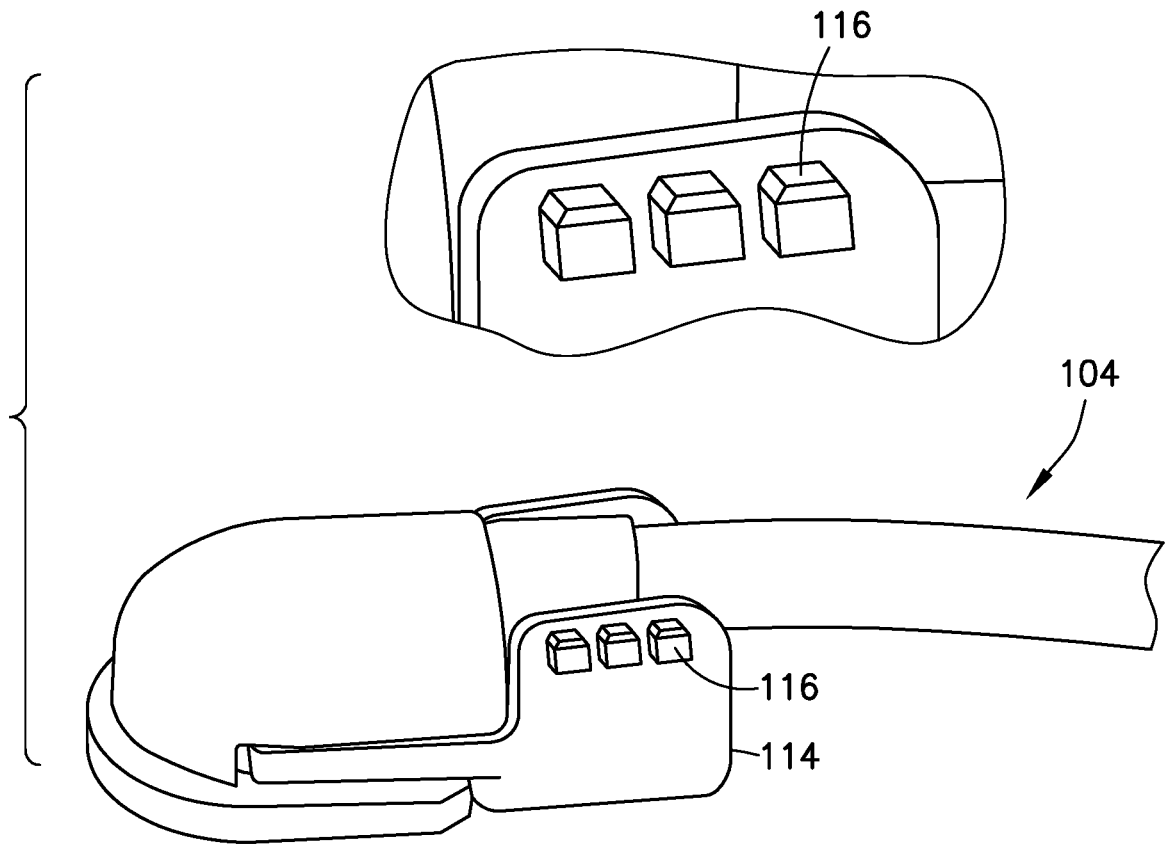
FIGS. 18-20 are respective perspective views of fluid connectors in accordance with other embodiments of the present invention.

As shown in FIG. 18, the activation lever 114 of the latching portion 104 includes a raised lateral tactile feature 116, which is disposed on a proximal portion of the activation lever 114. The raised lateral tactile feature 116 helps prevent distal slippage of the fluid connector 100 from the user's grasp. The raised lateral tactile feature 116 also aids a user in lifting the fluid connector off the base 80. According to one embodiment, the raised lateral tactile feature 116 is a plurality of laterally cantilevered posts 116. According to one embodiment, the plurality of laterally cantilevered posts 116 include a plurality of laterally cantilevered polygons, such as those shown in FIG. 18. According to another embodiment (not shown), the plurality of laterally cantilevered posts 116 include a plurality of laterally cantilevered rectangular posts.

Figure 19:
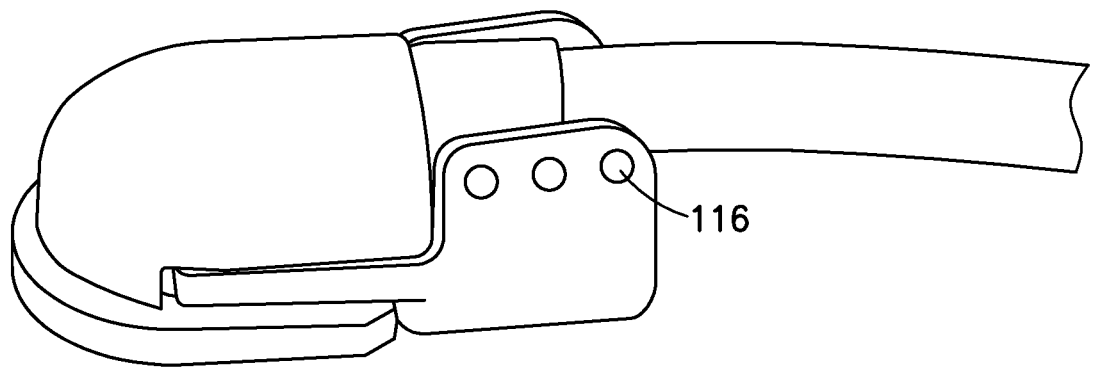
Figure 20:
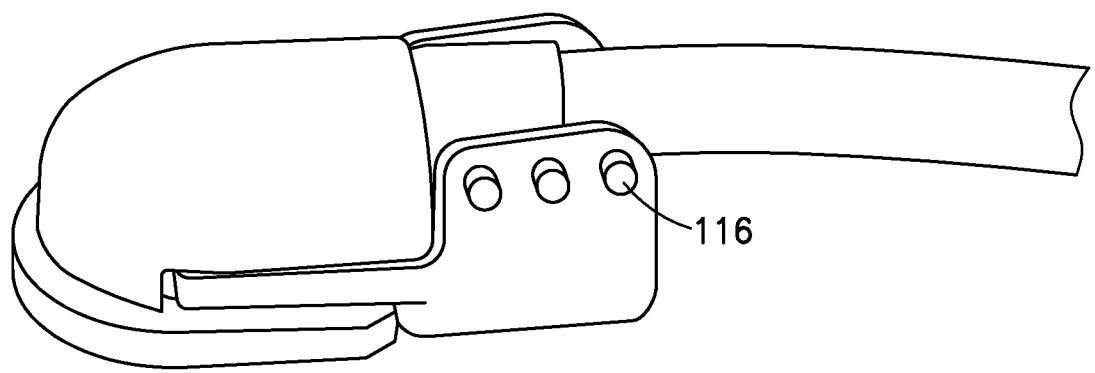

As shown in FIG. 19, the raised lateral tactile feature 116 can include a plurality of rounded bumps 116, and as shown in FIG. 20, the raised lateral tactile feature 116 can include a plurality of cantilevered cylindrical posts 116.

Figure 21:
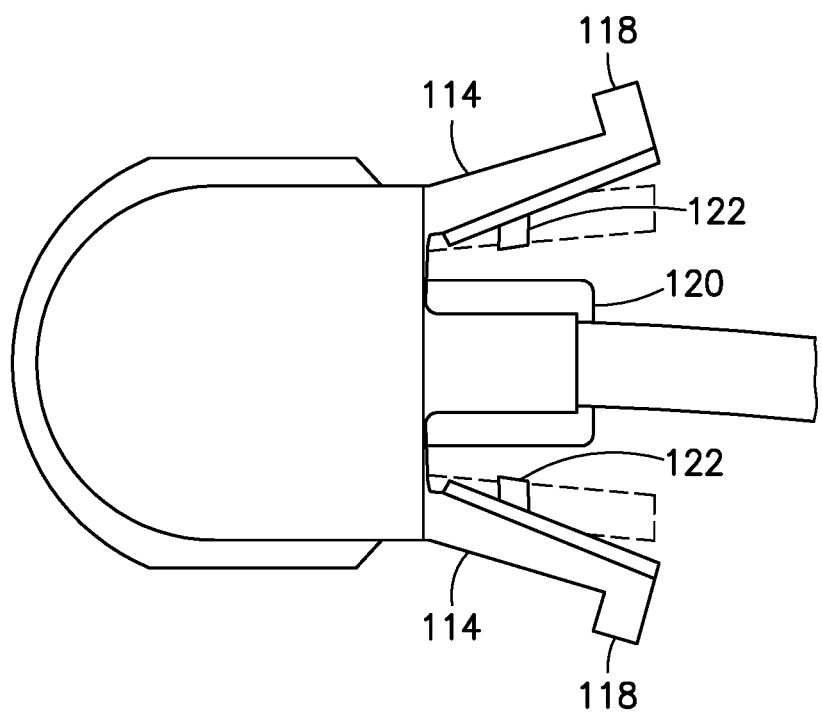
FIGS. 21 and 22 are respective top and perspective views of a fluid connector in accordance with another embodiment of the present invention.
Figure 22:
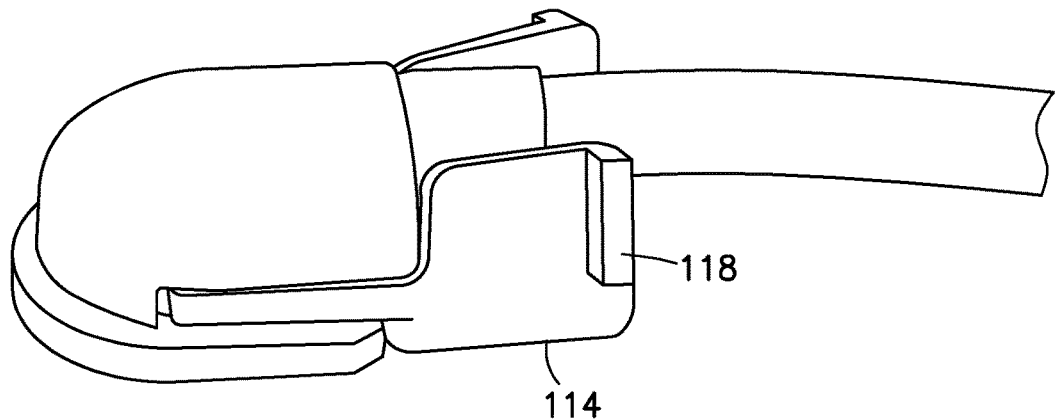

FIGS. 21 and 22 illustrate an embodiment in which the activation levers 114 each include a raised lateral tactile feature 118 disposed at respective rearmost portions of the activation levers 114. According to one embodiment, the raised lateral tactile feature 118 includes a vertical ridge 118 to prevent forward slippage of the fluid connector 100 from the user's grasp. One skilled in the art will appreciate shapes other than a vertical ridge can be employed without departing from the present invention's scope.

In FIG. 21, the unbiased or resting position of the activation lever 16 of the related art fluid connector 10 is shown in dotted lines. As can be seen in FIG. 21, the unbiased position of the activation levers 114 is splayed outward with respect to the unbiased position of the related art activation levers 16. In addition, the rigid stop 120 is laterally wider than the rigid stop 20 of the related art fluid connector 10, and the activation levers 114 have laterally inward protrusions 122. The wider rigid stop 120 and the laterally inward protrusions 12 combine to provide an inwardly squeezed or releasing position in which the activation levers are approximately parallel, or slightly beyond parallel. In comparison to a V-shaped releasing position with the related art activation levers 16, the new configuration also helps prevent forward slippage of the fluid connector 100 from the user's grasp.

Figure 23:
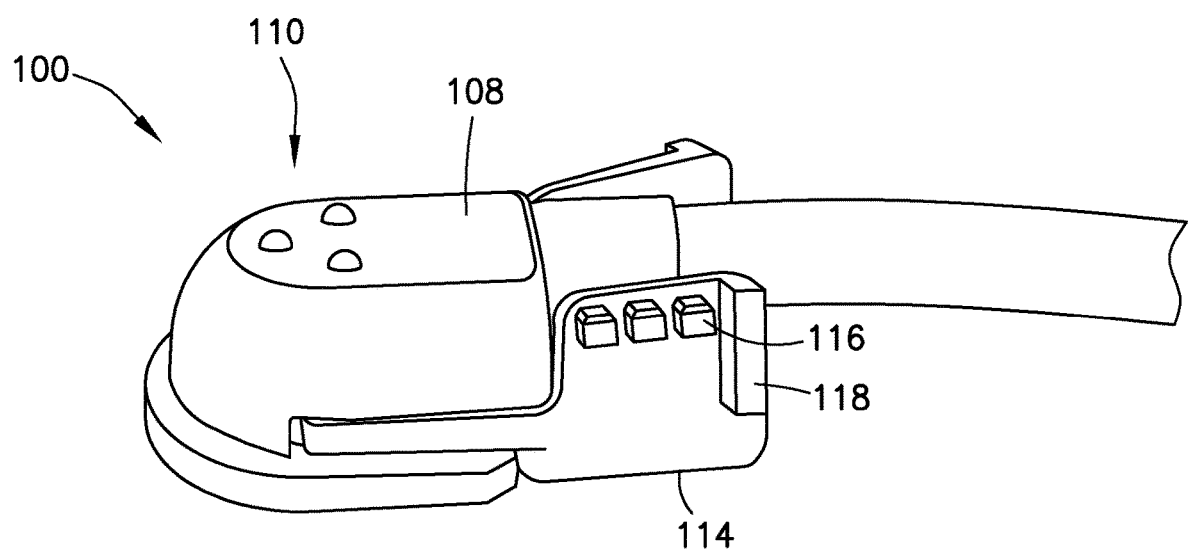
FIG. 23 is a perspective view of a fluid connector in accordance with another embodiment of the present invention.

As shown in FIG. 23, the fluid connector 100 can include a combination of features for aiding positioning of the fluid connector and preventing slippage from a user's grasp. For example, the fluid connector can include a flattened portion 108 with a raised tactile feature 110 disposed thereon, and the activation levers 114 can include laterally cantilevered polygons 116 and a vertical ridge 118. In addition, at rest, the activation levers 1147 can be splayed laterally outwardly in comparison to the related art activation levers 16. One skilled in the art will appreciate that other combinations of features can be employed without departing from the present invention's scope.

Although only a few embodiments of the present invention have been shown and described, the present invention is not limited to the described embodiments. It will be appreciated by those skilled in the art that other changes may also be made to the disclosed embodiments without departing from the scope of the invention. In addition, any of the embodiments, features and/or elements disclosed herein may be combined with one another to form various additional combinations not specifically disclosed, as long as the embodiments, features and/or elements being combined do not contradict each other. All such changes and combinations are considered to be within the scope of the invention as defined by the appended claims and their equivalents

What is claimed is:
1. A fluid connector for use with an infusion set, the fluid connector comprising:
a fluid path portion, comprising a cannula integral with and extending distally along a first axis from a proximal interior surface of the fluid path portion; and a latching portion secured to the fluid path portion and having a pair of displaceable arms, each arm comprising:
   a connector latch disposed at a first, cantilevered end of the arm; and
   an activation lever disposed at an opposite cantilevered end of the arm and extending along a second axis, not parallel to the first axis, wherein a rearmost portion of the activation lever includes a first lateral tactile feature comprising a ridge having a major axis aligned substantially parallel to the first axis, and a proximal portion of the activation lever includes a second lateral tactile feature aligned along an axis substantially parallel to the second axis that intersects the major axis of the first lateral tactile feature to form an "L" shape therewith to prevent slippage of the fluid connector from a user's grasp, the first and second lateral tactile features extending from the activation lever substantially parallel to a third axis that is not parallel to the first or second axes.

2. The fluid connector according to claim 1, wherein the second lateral tactile feature comprises a plurality of laterally cantilevered posts, each post extending laterally outward and having a central axis substantially perpendicular to the first and second axes.

3. The fluid connector according to claim 2, wherein the laterally cantilevered posts are substantially rectangular solids.

4. The fluid connector according to claim 2, wherein the laterally cantilevered posts are substantially cylindrical.

5. The fluid connector according to claim 2, wherein the laterally cantilevered posts are laterally cantilevered polygons.

6. The fluid connector according to claim 1, wherein a proximal exterior surface of the fluid path portion has a flattened portion substantially parallel to the second axis and has a third tactile feature centered about a longitudinal axis of the cannula to aid a user in connecting the fluid connector with an infusion set base.

7. The fluid connector according to claim 1, wherein the first axis is substantially perpendicular to the second axis.

8. The fluid connector according to claim 1, wherein:
   the fluid path portion includes a stop fixedly disposed thereon;
   the activation levers each include a lateral inward protrusion; and
   the lateral inward protrusions and the stop are configured to reach a releasing position in which the activation levers contact the stop and are substantially parallel.

9. The fluid connector according to claim 6, wherein the third tactile feature comprises three bumps arranged in a triangle centered about the longitudinal axis of the cannula.

10. The fluid connector according to claim 6, wherein the third tactile feature comprises a ring centered about the longitudinal axis of the cannula.

11. The fluid connector according to claim 6, wherein the raised third feature comprises a plurality of concentric rings centered about the longitudinal axis of the cannula.

12. The fluid connector according to claim 6, wherein the third tactile feature comprises a cross centered about the longitudinal axis of the cannula.

13. The fluid connector according to claim 6, wherein the third tactile feature comprises an "X" centered about the longitudinal axis of the cannula.

14. The fluid connector according to claim 6, wherein the third tactile feature comprises crosshairs centered about the longitudinal axis of the cannula.

15. The fluid connector according to claim 6, wherein the third tactile feature comprises a plurality of linear ribs centered about the longitudinal axis of the cannula.

16. The fluid connector according to claim 6, wherein the third tactile feature comprises a plurality of arcuate ribs centered about the longitudinal axis of the cannula.

17. A fluid connector, comprising:
   a fluid path portion, comprising a cannula integral with and extending from an interior surface of the fluid path portion; and
   a latching portion secured to the fluid path portion and having a pair of displaceable arms, each arm comprising:
      a connector latch disposed at a first cantilevered end of the arm; and
      an activation lever disposed at an opposite cantilevered end of the arm, wherein the activation lever includes a first lateral tactile feature aligned along a first axis, and a second lateral tactile feature having a major axis that forms an "L" shape with the first axis, to prevent slippage of the fluid connector from a user's grasp in multiple directions, wherein the first and second lateral tactile features extend from the activation lever substantially parallel to a third axis that is not parallel to the first and major axes.

* * * * *

UNITED STATES PATENT AND TRADEMARK OFFICE
CERTIFICATE OF CORRECTION

Page 1 of 1

PATENT NO. : 11,690,992 B2
APPLICATION NO. : 16/697765
DATED : July 4, 2023
INVENTOR(S) : Rachael Turner Kelly et al.

It is certified that error appears in the above-identified patent and that said Letters Patent is hereby corrected as shown below:

On the Title Page

In Column 1, item (72) inventors: correct the ninth inventor's last name from "Bums" to -- Burns --

Signed and Sealed this
Twenty-sixth Day of September, 2023

Katherine Kelly Vidal
*Director of the United States Patent and Trademark Office*